United States Patent [19]
Kostka et al.

[11] Patent Number: 6,039,966
[45] Date of Patent: Mar. 21, 2000

[54] AGROCHEMICAL EMULSION CONCENTRATES

[75] Inventors: Stanley J. Kostka, Cherry Hill; Rennan Pan, Plainsboro, both of N.J.

[73] Assignee: Aquatrols Corporation of America, Inc., Cherry Hill, N.J.

[21] Appl. No.: 09/212,995

[22] Filed: Dec. 16, 1998

Related U.S. Application Data

[60] Provisional application No. 60/070,101, Dec. 30, 1997.

[51] Int. Cl.[7] .......................... A01N 25/00; A01N 57/00; A01N 43/40; A01N 43/36
[52] U.S. Cl. .......................... 424/405; 504/195; 504/244; 504/287; 504/352
[58] Field of Search ............................ 514/127; 424/405; 504/195, 244, 287, 352

[56] References Cited

U.S. PATENT DOCUMENTS

| | | | |
|---|---|---|---|
| 4,868,206 | 9/1989 | Hobbs | 514/457 |
| 4,952,401 | 8/1990 | Hobbs | 424/405 |
| 5,045,109 | 9/1991 | Nakamura et al. | 71/100 |

FOREIGN PATENT DOCUMENTS

| | | | |
|---|---|---|---|
| 669078 | 2/1994 | European Pat. Off. | |
| 669 078 | 8/1995 | European Pat. Off. | A01N 25/02 |
| 670 113 | 9/1995 | European Pat. Off. | A01N 25/04 |
| 2048675 | 12/1980 | United Kingdom | |
| 9534200 | 12/1995 | WIPO | |

*Primary Examiner*—Jose' G. Dees
*Assistant Examiner*—Alton Pryor
*Attorney, Agent, or Firm*—John A. Shedden

[57] ABSTRACT

A low volatile organic compound co-solvent system is disclosed for preparing emulsion concentrates of water-insoluble pesticides having a melting point of less than about 110° C. The co-solvent system comprises a water-soluble ethoxylated fatty acid/rosin acid-nonionic surfactant composition.

11 Claims, No Drawings

6,039,966

AGROCHEMICAL EMULSION CONCENTRATES

This application claims the benefit of Provisional Appln No. 60/070,101 filed Dec. 30, 1997.

BACKGROUND OF THE INVENTION

1. Field of the Invention

The instant invention relates to highly concentrated, low volatile organic compound (low VOC) aqueous agrochemical compositions and methods for preparing same.

2. Technology Description

When agrochemical actives are relatively water soluble, preparing, storing, and shipping same in a commercially acceptable form can be a relatively simple matter. However, many, if not most, agrochemical actives are not very water soluble and formulators are constantly using their ingenuity to find means for preparing these materials in stable formulations that deliver maximum loading of active ingredient per unit volume to the end-user. One means of doing this is to prepare dry formulations such as wettable dispersible granules (WDG's) or wettable powders (WP's) encapsulated, for example, in water soluble bags or containers. Although such dry formulations are attractive not only from a loading delivery viewpoint, but also from a handling and/or worker safety viewpoint, not all water insoluble agrochemicals are able to be dry formulated.

The most straight-forward approach to preparing concentrated liquid formulations with agrochemical actives, e.g., pesticides having limited aqueous solubility, has been through the use of aromatic organic solvent systems. In such systems, aromatic organic solvents such as xylene or kerosene are used to solubilize the pesticidal compound of interest.

Commonly, surfactants are added to the pesticide-solvent compositions to form emulsions. The surfactant-emulsifiers interact with the pesticides in a number of ways both before and during actual use, i.e., application to the site. The surfactants, usually a pair of nonionic and anionic surfactants, can initially disperse and/or emulsify the pesticide in the solvent or in an inert carrier media and, for example, with herbicides, the surfactant composition may also act as a penetrant, spreader, sticker, stabilizer, wetting agent, and defoamer. The surfactant composition may affect the rate of drying of a droplet on a plant and the nature of a residue liquid, or crystal. The surfactants may also influence the weathering characteristics of a pesticide, including its rewetting characteristics.

The presence of the volatile organic compounds in these formulations, together with the surfactants, enable stable emulsifiable pesticidal concentrates (EC's) to be prepared. Although such EC formulations have played and continue to play a major role in the pesticidal market, they have a significant drawback in that the formulations are commonly based on the use of considerable quantities of the highly volatile organic compounds (high VOC's). These high VOC's create both toxicological and ecotoxicological problems. As a result, many government agencies such as the United States Environmental Protection Agency and the European Economic Community Council are proposing legislation and many countries such as Germany and Canada are now requiring eco-labeling of formulations which contain high VOC's.

Thus, to reduce not only the deleterious effects upon the environment, but also the potential for hazardous worker exposure situations, especially in closed environments such as greenhouses, agricultural/chemical manufacturers and formulators continually seek ways to deliver highly loaded, stable agrochemical active formulations to the end-user with significantly reduced levels of high VOC's and preferably without their presence.

To avoid the use of high VOC's in certain pesticidal formulations, Lubetzky, et al. in EP publication numbers 669,078 and 670,113 have disclosed the use of rosin and rosin derivatives that are insoluble in water to "plasticize" certain pesticides and thus to prepare pesticidal emulsions in water (EW's) and emulsifiable concentrates (EC's). By the term "rosin derivatives insoluble in water" Lubetzky, et al. include "hydrogenated rosin, polymerized rosin, methyl esters of rosin or of hydrogenated rosin, glycerol esters of rosin or hydrogenated rosin, triethylene glycol esters of rosin or hydrogenated rosin and pentaerythratol esters of rosin or hydrogenated rosin". By utilizing the above-identified rosin and rosin derivatives as plasticizers, Lubetzky, et al. are apparently able to slightly increase the pesticidal loadings in the EW's and EC's above that realizable in standard high VOC formulations.

It would be very desirable to be able to provide agrochemical formulators with the means to prepare aqueous pesticidal emulsions from stable water-soluble pesticidal emulsion concentrates having very high pesticide loading levels in the absence of environmentally unfriendly, highly volatile organic compounds.

SUMMARY OF THE INVENTION

This invention relates to stable water-soluble, low VOC pesticidal emulsion concentrates comprising a) a pesticide having a melting point of 110° C. or less; b) a solvent for said pesticide comprising an alkoxylated fatty acid and rosin acid composition having from greater than about 25 to about 60 weight percent alkoxylated rosin acids and from about 40 to less than about 75 weight percent alkoxylated fatty acids—the weight percents of the fatty acids and rosin acids being based on the total weight of the alkoxylated acid composition wherein the alkoxylated composition contains an average molar addition of from about 9 to 20 alkoxy moieties per molecule of acid; and c) at least one nonionic surfactant.

DETAILED DESCRIPTION OF THE INVENTION

It has been discovered that certain water-soluble fatty acid/rosin acid ethoxylate compositions possess very unique solvent characteristics with respect to certain water insoluble pesticides. Specifically, it has been discovered that water insoluble pesticides having low to medium melting points can be melted and readily dissolved in a low VOC water-soluble solvent prepared by highly alkoxylating a mixture of fatty acids and rosin acids; preferably a tall oil mixture.

The primary fatty acids useful in the process of this invention are the $C_{14}$ to $C_{20}$ unsaturated acids, especially the fatty acids selected from the group consisting of oleic, linoleic, conjugated linoleic acids, palmitic, stearic, and mixtures thereof.

The primary rosin acids useful in the process of this invention are the $C_{19}$–$C_{20}$ aromatic acids, especially the rosin acids selected from the group consisting of abietic, neoabietic, dehydroabietic, tetrahydroabietic, palustric, pimaric acids and mixtures thereof.

The final acid compositions, whose components are subsequently alkoxylated either prior to being mixed together to form the composition or after the acid composition mixture is present, comprise from greater than about 25 to about 60 weight percent alkoxylated rosin acids, preferably from 30 to 40 weight percent alkoxylated rosin acid; and from about 40 to less than about 75 weight percent, preferably from about 60 to about 70 weight percent fatty acids; all of the above acid weight percents based on the total weight of the alkoxylated fatty acids and rosin acids composition.

The water-soluble alkoxylated compositions should contain an average molar addition of from about 6 to about 20 alkoxy moieties per molecule of acid; preferably from about 9 to about 16.

As noted above, although the rosin acids can be obtained individually from natural products such as wood and gum resins and the fatty acids can be obtained individually, for example, from natural oils and fats such as olive oil, peanut oil, butter fat, cottonseed, soybean and so on, the fatty acid/rosin acid compositions of this invention are preferably obtained from certain tall oil products.

The pine tree is the source of tall oil which is liberated when wood is converted to paper pulp by the sulfate or Kraft process. During the pulping process, an alkaline digestion liquor ("black liquor") is washed out of the pulp. Rosin soaps and fatty acid soaps are skimmed off of this black liquor and acidification releases free rosin and fatty acids. This mixture was originally called Tallolja (Swedish for pine oil) and the term "tall oil" was eventually adapted as a standard by the United States.

The fatty acids in crude tall oil typically consist mainly of a mixture of oleic acid [40.0%] [$CH_3$ $(CH_2)_7CH=CH$ $(CH_2)_7COOH$]; linoleic acid [32.0%] [$CH_3(CH_2)_4CH=CH$ $CH_2$ $CH=CH$ $(CH_2)_7$ $COOH$]; linoleic acid, conjugated (includes higher molecular weight polyunsaturated acids) [10.0%] [$CH_3(CH_2)_4$ $CH_2$ $CH=CH$ $CH=CH$ $(CH_2)_7$ $COOH$]; palmitic acid [6.5%] [$CH_3(CH_2)_{14}$ $COOH$]; and stearic acid [2.0%] [$CH_3$ $(CH_2)_{16}$ $COOH$]. Also present are palmitoleic acid [1.5%]; and to a small extent, higher molecular weight saturated acids such as arachidic ($C_{20}$), behinic ($C_{22}$), lignoceric ($C_{24}$) and cerotic ($C_{26}$) acids, $C_{20}$ and higher molecular weight unsaturated and polyunsaturated acids, and small amounts of low boiling monobasic and dibasic acids.

The rosin acids in crude tall oil are similar to those occurring in wood and gum rosin and typically consist mainly of abietic acid [30–40%] in equilibrium with its isomer neoabietic acid [4–20%], palustric acid [7%], dehydroabietic acid [5–17%], pimaric acid [8–16%], with dehydroabietic and tetrahydroabietic acids comprising 2 to 28%.

The fatty acid/rosin acid compositions of this invention are alkoxylated, i.e., polyoxyalkylene esters are prepared, by using art-recognized, standard condensation techniques readily available; known to those skilled in the art; and described in numerous publications, for example, on pages 142 to 170 of chapter 5 of the book "Nonionic Surfactants" by W. B. Satkowski, S. K. Huang, and R. L. Liss, edited by M. J. Schick, Lever Bros. Co. Research Center, Edgewater, N.J. (Marcel Dekker, Inc., New York). Typical procedures are set forth in U.S. Pat. Nos. 2,586,767 and 2,610,966.

The organic carboxylic acids may be either directly esterified with alkylene oxide or through a reaction with polyalkylene glycol intermediates. The alkylene oxides which may be used to prepared the nonionic monofunctional polyoxyalkylene esters or polyalkylene glycol intermediates include ethylene oxide, propylene oxide and butylene oxide. Tetrahydrofuran may also be used. Preferred alkylene oxides are ethylene oxide and propylene oxide. When both of these oxides are utilized, they may be added simultaneously or in sequence to prepare statistic or block polymer surfactants. The alkylene oxides, for example, ethylene oxide, may also be used alone.

Pesticides which are useful in the formulations of this invention are those that have a melting point under 110° C.; preferably under 90° C. Suitable pesticides can be selected for example from the following classes of pesticidally active substances:

acetanilides
benzoates
benzofurans
chlorinated hydrocarbons
hydroxybenzonitriles
imidazoles
nitroanilines
nitroxylenes
organophosphorous compounds
oxidiazoles
phenoxy-phenoxy-alkane-carboxylic acid derivatives
pyrethroids and
triazoles Suitable acetanilides are in particular compounds of the type described in U.S. Pat. Nos. 3,442,945 and 3,547,620, especially 2-chloro-2'6α-diethyl-N-(methoxymethyl)-acetanilide (alachlor). Suitable benzoates are in particular compounds of the type described in Great Britain patent number 1,247,817 especially 3-chloro-ethoxyimino-2,6-dimethyloxybenzyl benzoate (benzoximate). Suitable benzofurans are in particular compounds of the type described in Great Britain patent number 1,271,659, especially 2-ethoxy-2,3-dihydro-3,3-dimethyl-5-benzofuranyl methane sulfonate (ethofumesate). Suitable chlorinated hydrocarbons are in particular compounds of the type described in U.S. Pat. No. 2,799,685, especially 6,7,8,9,10,10-hexachloro-1,5,5a,6,9,9a-hexahydro-6,9-methano-2,4,3-benzo-dioxathiepin-3- oxide (endosulfan). Suitable hydroxybenzonitriles are in particular compounds of the type described in U.S. Pat. Nos. 3,397,054 and 4,332,613, especially the esters of 3,5-dibromo4-hydroxyphenyl cyanide (bromoxynil) and 3,5-diiodo-4-hydroxyphenyl cyanide (ioxynil). Suitable imidazoles are in particular compounds of the type described in Great Britain patent number 1,469, 772, especially N-propyl-N-[2-(2,4,6-trichlorophenoxy)-ethyl]-1H-imidazole-1-carboxamide; also compounds described in U.S. Pat. No. 3,658,813, especially 1-[2-(2,4-dichlorophenyl)-2-(2-propenyloxy)-ethyl]-1H-imidazole (imazalil). Suitable nitroanilines are in particular compounds of the type described in U.S. Pat. No. 3,257,190, especially N-butyl-N-ethyl-2,6-dinitro4-trifluoromethyl-aniline (benfluralin) or 2,6-dinitro-N,N-dipropyl-4-trifluoromethyl aniline (trifluralin). Suitable nitroxylenes are in particular compounds of the type described in U.S. Pat. No. 3,385,862, especially N-1(1-ethylpropyl)-2,6-dinitro-3,4-xylidine (pendimethalin). Suitable organophosphorous compounds are in particular compounds of the type described in U.S. Pat. No. 3,244,586, especially O,O-diethyl-O-(3,5,6-trichloro-2-pyridyl)-phosphorothioate (chlorpyrifos ethyl) and O,O-dimethyl-O-(3,5,6-trichloro-2-pyridyl)-phosphorothioate (chlorpyrifos methyl); also the compounds described in Great Britain patent number 974,138, especially 1,3-dithiolan -2-ylidene-phosphorimidate (phospholan); also the compounds described in U.S. Pat. Nos. 3,230,230 and 3,240,668, especially S-[{5-methoxy-2-oxo-1,3,4-thiadiazol-3-(2H)-yl}-methyl]-O,O-dimethylphosphorodithioate (methidathion); also the compounds described in U.S. Pat. No. 3,205,253, especially O,O-diiso-propyl-S-2-phenyl-sulphonyl-aminoethyl-phosphoro-dithioate (bensulfide); also the compounds described in U.S. Pat. No. 2,978,479, especially ethyl-3-methyl-4-(methylthio)-phenyl-isopropyl-phosphoramodate (fenamiphos). Suitable oxidiazoles are in particular compounds of the type described in U.S. Pat. No. 3,385,862 especially 3-[2,4-dichloro-5-(1-methyl-ethoxy)-phenyl]-5-(1,1-dimethyl-ethyl)-1,3,4-oxadiazole-2-(3H)-one (oxadiazon). Suitable phenoxy-phenoxy-alkane-carboxylic acid derivatives are in particular compounds of the type described in West German patent number 2,136,828 and 2,223,804, especially methyl-2-[4-(2,4-dichlorophenoxy)-phenoxy]-propanoate (diclofop methyl). Suitable pyrethroids are in particular compounds of the type described in Great Britain patent number 1,413,491 especially (3-phenoxy-phenyl)-methyl-3-(2,2-dichloroethenyl)-2,2-dimethyl-cyclopropane-carboxylate (permethrin) and cyano-(3-phenoxy-phenyl)-methyl-3-(2,2-dichloroethenyl)-2,2-dimethyl-cyclopropane-carboxylate (cypermethrin); also 2-methyl-biphenyl-3-yl-methyl-(Z)-(IRS)-cis-3-(2-chloro-3,3,3-trifluoro-prop-1-enyl)-2,2-dimethyl-cyclopropane-carboxylate (bifenthrin); also the compounds described in U.S. Pat. No. 4,062,698, especially cyano-(3-phenoxy-phenyl)-methyl-(RS)-2-(4-chloro-phenyl)-3-methyl butyrate (fenvalerate). Suitable triazoles are in particular compounds of the type described in Israel patent number 73,450, especially 2-(4-chlorophenyl)-2-(1H)-(1,2,4-triazole-1-yl-methyl) hexanitrile (myclobutanil); also the compounds described in Great Britain patent number 1,522,657, especially 1-[2-(2,4-dichlorophenyl)-4-propyl-1,3-dioxolan-2-yl-]-methyl-1H-1,2,4-triazole (propiconazole).

The preferred pesticidal actives include dithiopyr (S,S'-dimethyl 2-(difluoromethyl)-4-(2-methylpropyl)-6-(trifluoromethyl)-3,5-pyridine dicarbothioate; chlorpyrifos (0,0-diethyl 0-(3,5,6-trichloro-2-pyridyl)-phosphorothioate; iprodione (3-(3,5-dichlorophenyl)-N-(1-methylethyl)-2,4-dioxo-1-imidazolidine carboxamide); and oxyfluorfen (2-chloro-1-(3-ethoxy-4-nitrophenoxy)-4-(trifluoro methyl benzene).

The nonionic surfactants useful in the formulations of this invention must have significant solubility in water. The H.L.B. of the nonionic surfactants should preferably be in the solubilizer/wetting agent range of from about 12 to about 20.

Examples of such nonionic materials are the following:
1) block-polymeric polyether glycols obtained, for example, by the addition of ethylene oxide on a condensation product of propylene oxide with propylene glycol;
2) alkoxylated alkyl phenols, i.e., alkylphenol-polyalkylene oxide condensates which are condensation products of alkylphenols with at least one alkylene oxide;
3) alkoxylated triglycerides;
4) alkoxylated di- or tri-styryl phenols;
5) alkoxylated sorbitol fatty esters;
6) condensation products of aliphatic alcohols with at least one alkylene oxide;
7) condensation products of ethylene oxide with the products resulting from the reaction of propylene oxide and ethylene diamine;
8) ammonia, monoethanol and diethanol amides of acyl fatty acids. These acyl moieties are normally derived from naturally occurring glycosides, but can be derived synthetically, and
9) various semi-polar, long chain nonionics including:
   i) tertiary amine oxides,
   ii) tertiary phosphine oxides; and
   iii) sulfoxides.

The preferred nonionic surfactants are the condensation products of aliphatic alcohols with at least one alkylene oxide and the alkoxylated alkyl phenols, especially the aliphatic ethoxylates and the alkylphenol polyethoxylates; the alkoxylated triglycerides such as ethoxylated and ethoxylated-propoxylated castor oil; and the alkoxylated sorbitol fatty esters. Most preferred are the alkylphenol ethoxylates which are alkylphenol-polyethylene oxide condensates of alkyl phenols having at least one alkyl group containing from 4 to 20, preferably 5 to 12 carbon atoms in either a straight chain or branched chain configuration on the phenol and condensed with ethylene oxide, the said ethylene oxide being present in amounts equal to 2 to 50 moles of ethylene oxide per mole of alkylphenol; preferably 5 to 25, most preferably 8–15. The alkyl substituent in such compounds may be derived from, but not limited to polymerized propylene, diisobutylene, amylene, octene, or nonene, for example.

Examples of compounds of this type include nonyl phenol condensed with about 9.5 moles of ethylene oxide per mole of nonyl phenol; dodecylphenol condensed with about 12 moles of ethylene oxide per mole of phenol, diamyl phenol condensed with about 9 moles of ethylene oxide per mole of phenol; dinonyl phenol condensed with about 15 moles of ethylene oxide per mold of phenol; and diisooctyl phenol condensed with about 15 moles of ethylene oxide per mole of phenol. Commercially available nonionic surfactants of this type include the IGEPAL series of nonionics, e.g., those sold under the trademarks CO-630 and DAP-9 by Rhodia Inc.

The primary components of the low VOC water-soluble, pesticidal emulsion concentrates of the instant invention have the following concentration ranges: the pesticide is present from 10 to 60 weight percent, preferably from 10 to 40 weight percent; the ethoxylated fatty acid/rosin acid mixture from 20 to 60 weight percent, preferably from 30 to 50 weight percent; and the nonionic surfactant from 15 to 45 weight percent, preferably from 20 to 40 weight percent; all weight percents being based on the total weight of the emulsion concentrate.

The liquid pesticide, ethoxylated fatty acid/rosin acid mixture, and nonionic surfactant concentrates, i.e., the water-soluble, low VOC compositions of this invention, can be used to prepare stable oil-in-water emulsions. When these emulsions in water (EW's) are desired, the preferred concentration ranges of the components based on the total weight of the aqueous emulsion are as follows: the pesticide should be present from 1 to 50 weight percent; the alkoxylated fatty acid/rosin acid composition should be present from 2 to 50 weight percent; and the nonionic surfactant from about 1.5 to 35 weight percent. The water can be present up to about 78 weight percent.

The ability of the concentrates of this invention to form stable emulsions when diluted with water is especially important for the solution stability allows for a homogeneous distribution of active ingredients on application targets, which results in enhanced biological efficacy.

The agrochemical compositions according to the invention may optionally comprise:
a) an anionic surfactant, such as i) partial sulfate and phosphate esters of polyoxyalkylene or (ii) carboxylate surfactants and their b) other nonionic surfactants, for example, polyoxyalkylene ethers of aliphatic alcohol having from 6 to 30, preferably from 10 to 20, and more particularly from 12 to 16 carbon atoms in the aliphatic residue; and/or c) a long chain carboxylic acid having from 10 to 25 carbon atoms such as caproic acid, caprylic acid, capric acid, lauric acid, myristic acid, palmitic acid, palmitoleic acid, margaric acid, stearic acid, oleic acid, linoleic acid, linolenic acid, and arachidic acid; and/or d) a lower alkanol ester of a long chain $C_{10}$–$C_{22}$ carboxylic acid, such as, for example, oleic, linoleic, linolenic, stearic, myristic, and palmitic acids; and/or e) an acidulated soap stock, said soap stock being a by-product of alkali refining of crude vegetable or animal fats and oils such as oils extracted from soybeans, canola, corn, cottonseed, olives, sunflower, safflower, sesame, peanut, rapeseed and rice; acidulated soybean soapstock being the preferred soapstock.

The agrochemical compositions of this invention may also comprise anti-freezing agents, anti-foam agents, compatibility agents, oxidation and U.V. protectants, bactericides, and pH buffering agents. Anti-foam agents decrease and/or prevent foaming when the solution containing the pesticidally-active formulation is agitated or sprayed. Compatibility agents function to allow and maintain an emulsification of two or more ingredients that would otherwise separate when mixed. Buffering agents function to moderate the pH of the water in the tank solution.

The concentrated formulations of this invention can be prepared preferably by melting one or more of the water-insoluble pesticidally-active ingredients and physically blending this molten material with the alkoxylated fatty acid/rosin acid solvent. The nonionic surfactant composition and any optional ingredients are then added to the mixture using standard emulsion preparation methods well known in the art. The sequence of addition is not a critical feature of the invention. Furthermore, the ingredients can also be premixed prior to the application of heat.

Other than in the operating examples, or where otherwise indicated, all numbers expressing quantities of ingredients or reaction conditions used herein are to be understood as modified in all instances by the term "about".

The following examples serve to illustrate, but not limit, the invention. All parts and percentages are by weight, unless otherwise noted.

EXAMPLE 1

Rosin acid-fatty acid (RFA) compositions having approximately the following composition: abietic acid (21–22 weight percent), palustric acid (2–3 weight percent), pimaric acid (7–8 weight percent), various isomers of the abietic, palustric and primaric acids and similar cyclic acids (6–7 weight percent), oleic acid (15–16 weight percent), linoleic acid (11–12 weight percent), isomers of $C_{18}$–$C_{19}$ and $C_{20}$ acids (9–10 weight percent), and dimer and higher fatty acids (17–18 weight percent) are ethoxylated such that a series of ethoxylated rosin acid-fatty acid compositions are prepared having a molar addition of approximately 9, 12, 16 and 20 ethylene oxide moieties per molecule of acid.

Varying amounts of dithiopyr, a pre-emergent herbicide, are blended with the above described compositions and the non-alkoxylated rosin acid-fatty acid starting composition as a control. The samples are heated in an oven to a temperature above the melting point of the dithiopyr, i.e., in the range of from about 65–70° C. After the herbicide has melted, the samples are well agitated and subsequently cooled to room temperature. The samples are not disturbed for three weeks at the end of which time observations are made on the solution solubilities. The results are as indicated in Table I.

TABLE I

Solubility of Dithiopyr in Ethoxylated Rosin-Fatty Acid Compositions at Room Temperature Three Weeks After Blending

| Dithiopyr (Weight Percent) | RFA (OEO) | RFA (9EO) | RFA (12EO) | RFA (16EO) | RFA (20EO) |
|---|---|---|---|---|---|
| 10 | NT* | ++ | NT | ++ | NT |
| 20 | -- | ++ | ++ | ++ | -- |
| 25 | -- | NT | NT | -- | NT |
| 30 | -- | -- | -- | -- | -- |
| 40 | -- | -- | -- | -- | -- |

*NT Not Tested; the dithiopyr was relatively insoluble in the blend.
++ Stable, One Phase
-- Unstable, Multi-Phased Solution
+/- Slight Crystal Formation Commercial dithiopyr concentrate loadings using highly volatile organic compound (high VOC) solvents typically are within the range of from about 10 to 14 weight percent ai; with most being in the range of from about 12 to 13 weight percent, based on the total weight of the concentrate.

The above results illustrate the significant increase in stable, single phase solubility that can be achieved for a moderate to low melting, water insoluble pesticide without VOC solvents via the use of rosin-fatty acid compositions that have been ethoxylated to yield RFA compositions having molar additions of from about 9 to about 16 ethylene oxide moieties per molecule of acid.

EXAMPLE II

A series of tests are conducted in a manner identical to the tests conducted in Example 1 except that chlorpyrifos is substituted for the dithiopyr pesticide utilized in that Example. The results are as indicated in Table II below.

TABLE II

Solubility of Chloroyrifos in Ethoxylated Rosin-Fatty Acid Compositions at Room Temperature Three Weeks After Blending

| Chlorpyrifos (Weight Percent) | RFA (9EO) | RFA (12EO) | RFA (16EO) | RFA (20EO) |
|---|---|---|---|---|
| 10 | NT | NT | ++ | NT |
| 20 | NT | NT | ++ | NT |
| 30 | NT | NT | ++ | NT |
| 40 | ++ | ++ | ++ | -- |
| 50 | ++ | ++ | +/- | -- |
| 60 | ++ | ++ | -- | -- |
| 70 | NT | NT | -- | NT |

As in Example I, maximum pesticidal solubilities and stability are realized with ethoxylation between about 9 and 16.

EXAMPLE III

Solutions are prepared as in Example I with four pesticides, i.e., chlorpyrifos, dithiopyr, oxyfluorfen, and iprodione at different weight percent loadings in the ethoxylated rosin-fatty acid composition of Example I having a molar addition of the ethylene oxide moiety per molecule of acid of about 16. The chlorpyrifos is an insecticide; the dithiopyr a pre-emergent herbicide; the oxyfluorfen a preand post-emergent herbicide; and the iprodione is a contact fungicide. As in Example I, the solutions are cooled to room temperature and stored undisturbed for three weeks at which time solubility/stability observations are made. The results are set forth in Table III.

TABLE III

Solubility of Various Pesticidal Compounds in RFA (16EO) at Room Temperature Three Weeks After Blending

| Weight Percent | Chlorpyrifos | Dithiopyr | Oxyfluorfen | Iprodione |
|---|---|---|---|---|
| 10 | ++* | ++ | ++ | ++ |
| 20 | ++ | ++ | ++ | ++ |
| 25 | NT | -- | NT | ++ |
| 30 | ++ | -- | ++ | -- |
| 40 | ++ | NT | -- | -- |
| 50 | +/- | NT | NT | -- |
| 60 | -- | NT | NT | NT |
| 70 | -- | NT | NT | NT |

*++ Stable, Single Phase Solution
-- Unstable, Multi-Phased Solution
NT Not Tested The above results illustrate that the water-soluble 16 EO ethoxylated rosin acid-fatty acid compositions of this invention can provide excellent stable solvents in the absence of highly volatile organic compounds (high VOC's) for a wide variety of water-insoluble pesticides.

EXAMPLE IV

Four samples are prepared by mixing in a weight ratio of 4:1, the RFA (9EO) composition of Example I with nonionic surfactant, namely, ethoxylated diamylphenol. The average ethylene oxide molar addition per mole of the diamylphenol is 9. Dithiopyr is blended into the RFA (9EO)/nonionic surfactant solvent system at various concentrations; heated; agitated; and cooled to room temperature as in Example I. The samples are stored for three weeks and solubility/stability observations made at the end of that time. The results are as set forth in Table IV.

TABLE IV

Solubility of Dithiopyr in a 4:1 (Weight:Weight) RFA (9EO):Diamylphenol (9EO) Solvent

| Dithiopyr (Weight Percent) | RFA (9EO):Diamylphenol (9EO) (4:1, Weight:Weight) |
|---|---|
| 10 | ++ |
| 20 | ++ |
| 25 | ++ |
| 30 | -- |

* ++ Stable, Single Phase Solution
-- Unstable, Multi-Phase Solution

The above results illustrate the synergistically increased solubility that can be realized above that of the ethoxylated RFA compositions alone (see Example I) when nonionic surfactant is present as a co-solvent/ solubility aid.

EXAMPLE V

Incrementally different amounts of chlorpyrifos are blended with 1) the rosin-fatty acid (16EO) ethoxylated composition of Example I; and 2) a 4:1 (weight:weight) blend of this RFA (16EO) with an ethoxylated nonylphenol (9EO) nonionic surfactant. These samples are heated in an oven to above the melting point of the chlorpyrifos. The samples are then well agitated and subsequently cooled to room temperature. The samples are left undisturbed for three weeks at the end of which time observations are made on the solution solubilities. The results are set forth in Table IV. Concentrations are indicated in pounds of active ingredient per gallon of total formulation, e.g., 5E represents 5 pounds a.i. per gallon of formulated product.

TABLE V

Chlorpyrifos Solubilities

| Chlorpyrifos Concentration | RFA (16EO) | RFA (16EO):NP9* (4:1, Weight:Weight) |
|---|---|---|
| 1E | ++ | ++ |
| 2E | ++ | ++ |
| 3E | ++ | ++ |
| 4E | ++ | ++ |
| 5E | +/- | ++ |
| 6E | -- | -- |

*Nonylphenol Ethoxylated with 9EO/Molecule (Av.)

Surfactants, primarily nonionics, are known to enhance the penetration and distribution of water and crop protection chemicals into the soil and rootzone. Serendipitously, when certain nonionic surfactants are co-formulated with the RFA ethoxylated compositions of this invention and used as co-solvent/stabilizers, the pesticidal loading levels can be increased and the stability of the overall formulations can be improved over that of the individual components.

EXAMPLE VI

Technical dithiopyr is melt blended into 1) the RFA (16EO) compositions of Example I; 2) a nonylphenol ethoxylate (9EO Av.); and 3) a 4:1 (Weight:Weight) blend of the RFA (16 EO) and the nonylphenol (9EO). Solution/stability observations are made after three weeks as described in Example I. The results are set forth in Table VI.

TABLE VI

Dithipyr Solubility

| Dithiopyr (Weight Percent) | NP* (9EO) | RFA (16EO) | RFA(16EO):NP(9EO) (4:1, Weight:Weight) |
|---|---|---|---|
| 10 | ++ | ++ | ++ |
| 20 | -- | ++ | ++ |
| 25 | -- | -- | ++ |
| 30 | -- | -- | -- |

*Nonylphenol Ethoxylate

The dithiopyr loading limit in the nonylphenol ethoxylate is about 10% in the rosin acid-fatty acid ethoxylate (16EO) about 20%; and in the rosin acid-fatty acid ethoxylate (16EO)—NP9 blend, it synergistically increased to about 25 weight percent.

EXAMPLE VII

Emulsion concentrates (EC's) of the instant invention with pesticidal compositions as indicated in Table VII below are prepared as in Example V. The compositions are then diluted with water in a 10 water to 1 EC ratio to form aqueous spray emulsions. Two commercial emulsion concentrates, both containing high VOC's, i.e., MICRO-FLO chlorpyrifos, a 2E emulsion concentrate trademark of the Micro Flo Company and DIMENSION IE, a trademark of Rohm & Haas for a 12.7 weight percent dithiopyr in a heavy aromatic petroleum naphtha emulsion concentrate, are similarly diluted to form aqueous spray emulsions.

The visual appearance and stability of the spray solutions, as determined by the appearance of a multi-phased solution, are as indicated in Table VII below.

TABLE VII

| Composition | Low VOC's | Appearance | Spray Emulsion Stability |
|---|---|---|---|
| Micro-Flo Chlorpyrifos 2E | No | Cloudy | <2 Hours |
| RFA (16EO)/NP9 Chlorpyrifos 2E | Yes | Cloudy | >24 Hours |
| Dimension IE (12.7% Dithiopyr) | No | Cloudy | 24 Hours |
| RFA (16EO) 20% Dithiopyr | Yes | Cloudy | 24 Hours |
| RFA (16EO)/NP9 25% Dithiopyr | Yes | Clear to Cloudy | 48 Hours |

Thus, the aqueous spray emulsions prepared from the low VOC emulsion concentrates of the instant invention exhibit improved stability as compared to standard, commercially available emulsion concentrates containing high VOC's.

In addition to the enhanced stability and solubility properties achieved by the liquid pesticidal emulsion concentrates of this invention, advantages of the instant low VOC pesticidal compositions include reduced worker exposure to high VOC's; greater options for shipping formulated pesticides; advantageous labeling options; and decreased regulatory issues.

Furthermore, it has also been observed that the instant formulations unexpectedly reduce the odor of odiferous pesticidally active ingredients. Formulations of chlorpyrifos in the ethoxylated fatty acid/rosin acid and/or ethoxylated fatty acid/rosin acid-nonionic surfactant solvent systems of this invention significantly reduce the odor of the pesticide in both the formulated emulsion concentrate and the diluted aqueous spray preparations. The odor reduction was apparent even when a low odor chlorpyrifos technical active material was used.

As is evident from the foregoing, various modifications are contemplated in the practice of the invention. Accordingly, the scope of the invention is defined in the following claims wherein:

What is claimed is:

1. An agrochemical emulsion concentrate comprising
   a) from about 10 to about 60 percent by weight of a water-insoluble pesticide having a melting point of less than about 110° C.;
   b) from about 20 to about 60 percent by weight of a water-soluble alkoxylated acid composition wherein said acid composition comprises:
      i) from greater than about 25 to about 60 percent by weight alkoxylated rosin acids; and
      ii) from about 40 to less than about 75 percent by weight alkoxylated fatty acids wherein the rosin acids and fatty acids have an average molar addition of from about 6 to about 20 alkoxy moieties per molecule of acid, the weight percents of the rosin and fatty acids being based on the total weight of said alkoxylated acids; and
   c) from about 15 to about 45 percent by weight of nonionic surfactant; wherein the emulsion concentrate having 20 weight percent of said pesticide, is stable at room temperature for at least three weeks and the weight percents are based on the total weight of the emulsion concentrate except where indicated.

2. The agrochemical emulsion concentrate of claim 1 wherein the pesticide is selected from the group consisting of:
   i) acetanilides;
   ii) benzoates;
   iii) benzofurans;
   iv) chlorinated hydrocarbons;
   v) hydroxybenzonitriles;
   vi) imidazoles;
   vii) nitroanilines;
   viii) nitroxylenes;
   ix) organophosphorous compounds;
   x) oxidiazoles;
   xi) phenoxy-phenoxy-alkane-carboxylic acid derivatives;
   xii) pyrethroids;
   xiii) triazoles; and
   xiv) mixtures thereof.

3. The agrochemical emulsion concentrate of claim 1 wherein the rosin acid is selected from the group consisting of:
   i) abietic acid;
   ii) neoabietic acid;
   iii) palustric acid;
   iv) dehydroabietic acid;
   v) pimaric acid;
   vi) tetrahydroabietic acid; and
   vii) mixtures thereof.

4. The agrochemical emulsion concentrate of claim 1 wherein the fatty acid is selected from the group consisting of:
   i) oleic acid;
   ii) linoleic acid;
   iii) conjugated linoleic acid;
   iv) palmitic acid;
   v) stearic acid; and
   vi) mixtures thereof.

5. The agrochemical emulsion concentrate of claim 1 wherein the nonionic surfactant is selected from the group consisting of:
   1) block-polymeric polyether glycols;
   2) alkoxylated alkyl phenols;
   3) alkoxylated triglycerides;
   4) alkoxylated di- or tri-styryl phenols;
   5) alkoxylated sorbitol fatty esters;
   6) condensation products of alphatic alcohols with at least one alkylene oxide;
   7) condensation products of ethylene oxide with the products resulting from the reaction of propylene oxide and ethylene diamine;
   8) Ammonia, monoethanol and diethanol amides of acyl fatty acids;
   9) Semi-polar, long chain nonionics selected from the group consisting of
      i) tertiary amine oxides;
      ii) tertiary phosphine oxides; and
      iii) sulfoxides; and
   10) mixtures thereof.

6. The agrochemical emulsion concentrate of claim 1 wherein
   a) the melting point of the water insoluble pesticide is less than about 90° C.;

b) the alkoxylated rosin acid is present from about 30 to about 40 percent by weight and the alkoxylated fatty acid is present from about 60 to about 70 percent by weight based on the alkoxylated rosin acid-fatty acid composition; and c) the nonionic surfactant is selected from the group consisting of alkoxylated aliphatic alcohols, alkoxylated alkyl phenols, alkoxylated triglycerides, alkoxylated di or tristyryl phenols, and alkoxylated sorbitol fatty esters.

7. The agrochemical emulsion concentrate of claim 1 wherein the pesticide is selected from the group consisting of dithiopyr, chlorpyrifos, iprodione, and oxyfluorfen.

8. The agrochemical emulsion concentrate of claim 1 wherein the rosin acid-fatty acid composition is ethoxylated to an average molar addition of from about 9 to about 16 ethylene oxide moieties per acid molecule.

9. The agrochemical emulsion of claim 6 wherein the nonionic surfactant is selected from the group consisting of nonylphenol ethoxylated with 9 ethylene oxide moieties (9EO) per nonylphenol molecule; ethoxylated diamylphenol (9EO); ethoxylated tributylphenol (9 EO); ethoxylated 2,4-ditertiary butyl phenol (9EO); and ethoxylated disecondary butylphenol (9EO).

10. A method of preparing agrochemical emulsion concentrates comprising the steps of:

i) blending
  a) from about 10 to about 60 percent by weight of a water-insoluble pesticide having a melting point of less than about 110° C.;
  b) from about 20 to about 60 percent by weight of a water-soluble alkoxylated acid composition wherein said acid composition comprises:
    i) from greater than about 25 to about 60 percent by weight alkoxylated rosin acids; and
    ii) from about 40 to less than about 75 percent by weight alkoxylated fatty acids wherein the rosin acids and fatty acids have an average molar addition of from about 6 to about 20 alkoxy moieties per molecule of acid; the weight percents of the rosin and fatty acids being based on the total weight of said alkoxylated acids; and
  c) from about 15 to about 45 percent by weight of nonionic surfactant; wherein the weight percents are based on the total weight of the emulsion concentrate except where indicated ii) heating said nonionic surfactant to above the melting point either prior to, during, or after the blending; and iii) cooling the emulsion concentrate so formed to ambient temperature; wherein the emulsion concentrate, having 20 weight percent of said pesticide, is stable at room temperature for at least three weeks.

11. A method of preparing agrochemical emulsion concentrates comprising the steps of:

i) melting from about 10 to about 60 percent by weight of a water-insoluble pesticide having a melting point of less than about 110° C.;

ii) blending the molten pesticide with from about 20 to about 60 percent by weight of a water-soluble alkoxylated acid composition wherein said acid composition comprises:
  a) from greater than about 25 to about 60 percent by weight alkoxylated rosin acids; and
  b) from about 40 to less than about 75 percent by weight alkoxylated fatty acids wherein the rosin acids and fatty acids have an average molar addition of from about 6 to about 20 alkoxy moieties per molecule of acid; the weight percents of the rosin and fatty acids being based on the total weight of said alkoxylated acids; and iii) admixing from about 15 to about 45 percent by weight of nonionic surfactant wherein the emulsion concentrate, having 20 weight percent of said pesticide, is stable at room temperature for at least three weeks and the weight percents are based on the total weight of the emulsion concentrate except where indicated.

* * * * *